(12) United States Patent
Schütz et al.

(10) Patent No.: US 7,579,142 B2
(45) Date of Patent: Aug. 25, 2009

(54) METHODS FOR PURIFICATION OF BACTERIAL CELLS AND COMPONENTS

(75) Inventors: Michael Schütz, Lappersdorf (DE); Renate Grassl, Regensburg (DE); Roman Meyer, Schmidmühlen (DE); Sibylle Frick, Zeitlarn (DE); Ingrid Robl, Regensburg (DE); Thomas Zander, Lappersdorf (DE); Stefan Miller, Regensburg (DE)

(73) Assignee: Profos AG, Regensburg (DE)

( * ) Notice: Subject to any disclaimer, the term of this patent is extended or adjusted under 35 U.S.C. 154(b) by 716 days.

(21) Appl. No.: 10/482,235

(22) PCT Filed: Jun. 24, 2002

(86) PCT No.: PCT/DE02/02302

§ 371 (c)(1),
(2), (4) Date: Jun. 15, 2004

(87) PCT Pub. No.: WO03/000888

PCT Pub. Date: Jan. 3, 2003

(65) Prior Publication Data

US 2004/0248298 A1   Dec. 9, 2004

(30) Foreign Application Priority Data

Jun. 24, 2001   (DE) ................. 101 29 815

(51) Int. Cl.
| | | |
|---|---|---|
| *C12Q 1/70* | (2006.01) | |
| *C12Q 1/00* | (2006.01) | |
| *G01N 33/53* | (2006.01) | |
| *G01N 33/554* | (2006.01) | |
| *G01N 33/563* | (2006.01) | |
| *G01N 33/543* | (2006.01) | |

(52) U.S. Cl. ................. 435/5; 435/4; 435/7.1; 435/7.2; 435/7.32; 435/235.1; 436/512; 436/518

(58) Field of Classification Search ............ 435/4, 435/5, 7.1, 7.32, 235.1
See application file for complete search history.

(56) References Cited

U.S. PATENT DOCUMENTS

| 5,876,925 | A | 3/1999 | Siegel | 435/5 |
|---|---|---|---|---|
| 6,033,878 | A | 3/2000 | Matsunaga | 435/69.7 |
| 6,284,470 | B1 | 9/2001 | Bitner et al. | 435/6 |
| 7,087,376 | B2 * | 8/2006 | Miller | 435/5 |

FOREIGN PATENT DOCUMENTS

| DE | 195 20 398 | 12/1996 |
|---|---|---|
| DE | 199 06 352 | 7/1999 |
| DE | 198 37 751 | 2/2000 |
| DE | 199 46 656 | 8/2000 |
| EP | 1 118 676 | 7/2001 |
| WO | WO 91/12079 | 8/1991 |
| WO | WO 93/17129 | 9/1993 |
| WO | WO 98/16541 | 4/1998 |
| WO | WO 98/51693 | 11/1998 |
| WO | WO 98/53100 | * 11/1998 |
| WO | WO 00/29562 | 4/2000 |
| WO | WO 01/53525 | 7/2001 |
| WO | WO 01/09370 | 8/2001 |

OTHER PUBLICATIONS

Bennett et al (Journal of Applied Microbiology, 1997, 83,259-265).*
Sun et al (Journal of Industrial Microbiological & Biotechnology 2000, 25, 273-275).*
Bennett et al (Journal of Applied Microbiology, 1997, 83, 259-265).*
Bachrach and Friedmann, "Practical procedures for the purification of bacterial viruses," *Appl. Microbiol.*, 22:706-715, 1971.
Bennet et al., "The use of bacteriophage-based systems for the separation and concentration of *salmonella*," *Journal of Applied Microbiology*, 83(2):259-265, 1997.
Burda et al., "Stability of bacteriophage T4 short tail fiber," *Biological Chemistry*, 381:255-258, 2000.
Caparon et al., Analysis of novel streptavidin-binding peptides, identified using a phage display library, shows that amino acids external to a perfectly conserved consensus sequence and to the presented peptides contribute to binding, *Molecular Diversity*, 1(4):241-246, 1996.
Goldberg and King, "Temperature sensitive mutants blocked in the folding or subunit assembly of the bacteriophage P22 tail spike protein:II active mutant proteins matured at 30° C.," *J. Mol. Biol.*, 145:633-651, 1981.
González et al., "Interaction of biotin with streptavidin. Thermostability and conformational changes upon binding," *J. Biol. Chem.*, 272(17):11288-11294, 1997.
Haukanes and Kvam, "Application of magnetic beads in bioassays," *BioTechnology*, 11(1):60-63, 1993.
Miller et al., Phage P22 tailspike: removal of headbinding domain unmasks effects of folding mutations on native-state thermal stability, *Prot. Sci.*, 7:2223-2232, 1998.
Miller et al., "Phage P22 tailspike protein: removal of head-binding domain unmasks effects of folding mutations on native-state thermal stability.," *Biochemistry*, 37:9160-9168, 1998.
Mitraki et al., "Review: conformation and folding of novel beta-structural elements in viral fibre proteins: the triple Beta-spiral and triple Beta-helix," *J. Struct. Biol.*, 137(1-2):236-247, 2002.
Savage et al., *Avidin-Biotin Chemistry: A Handbook*, Pierce, Illinois, 1992.
Seckler, "Folding and function of repetitive structure in the homotrimeric phage P22 tailspike protein," *Journal of Structural Biology*, 122:216-222, 1998.
Seeley and Primrose, "The isolation of bacteriophages from the environment," *J. Appl. Bacteriol.*, 53:1-17, 1982.

(Continued)

Primary Examiner—Robert B. Mondesi
Assistant Examiner—Vanessa L. Ford
(74) Attorney, Agent, or Firm—Fulbright & Jaworski, LLP

(57) ABSTRACT

The present invention relates to a method for the selective purification of bacterial cells and/or cell components, whereby the purification is performed by means of a solid support.

5 Claims, 8 Drawing Sheets

OTHER PUBLICATIONS

Figure 1:
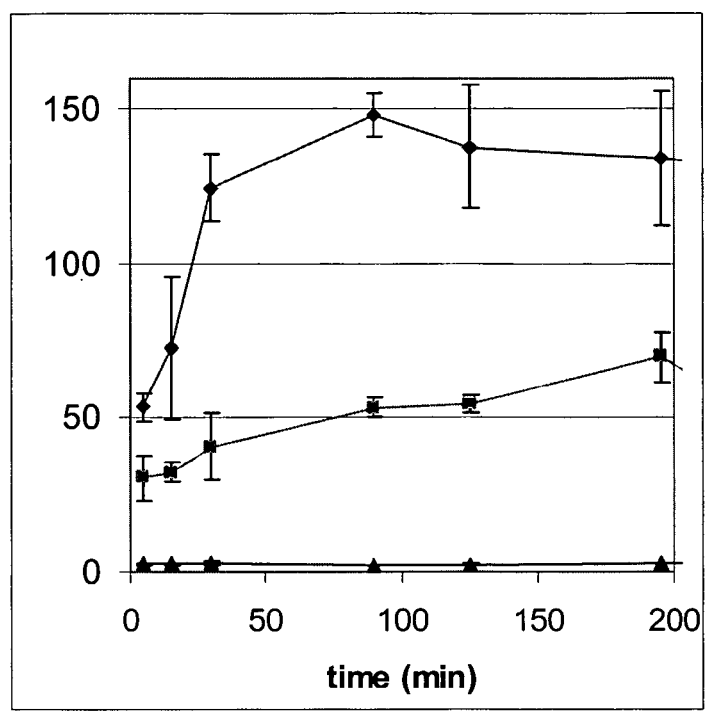

Selivanov et al., "Nucleotide and deduced amino acid sequence of bacteriophage T4 gene 12," *Nucleic Acids Research*, 16(5), Accession No. X06729, 1988.

Skerra and Schmidt, "Applications of a peptide ligand for streptavidin: the Strep-tag," *Biomolecular Engineering*, 16:79-86, 1999.

Sun et al., "Use of bioluminescent *Salmonella* for assessing the efficiency of constructed phage-based biosorbent," *Journal of Industrial Microbiology & Biotechnology*, 25(5):273-275, 2000.

Šafařík et al., "Use of magnetic techniques for the isolation of cells" *Journal of Chromatography*, 722: 33-53, 1999.

* cited by examiner

Fig. 5
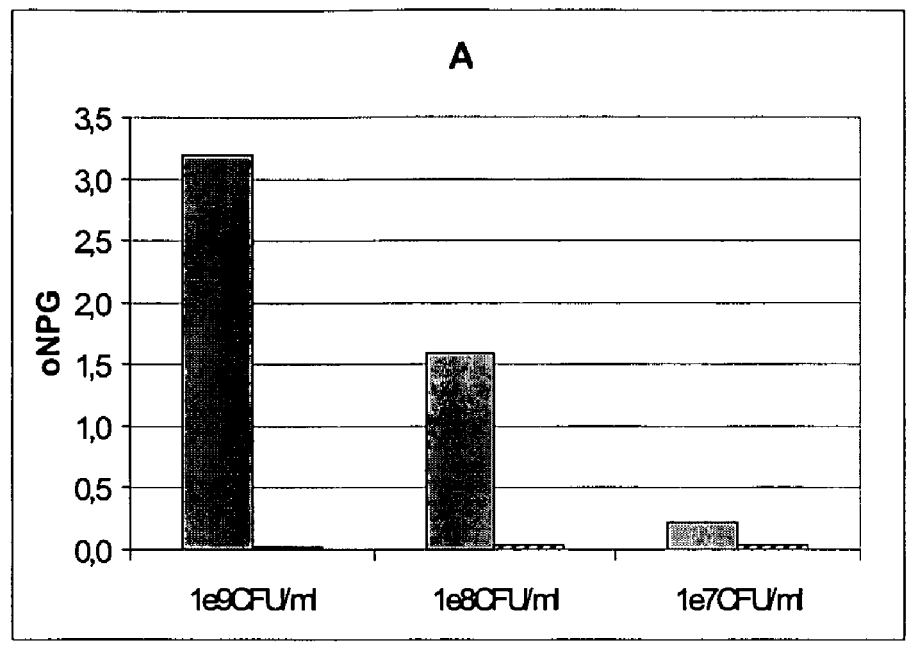
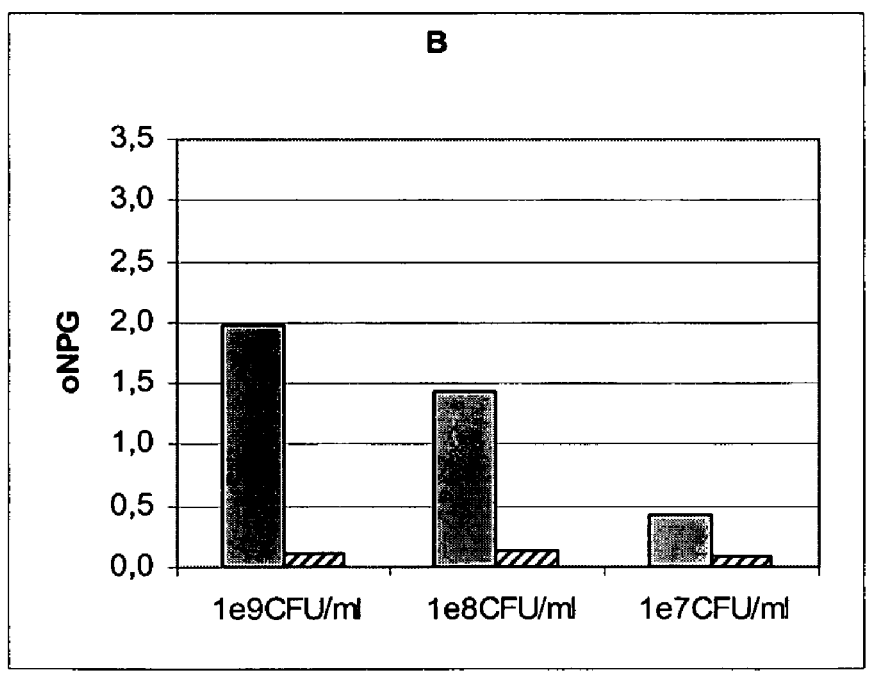

Fig. 7

A

| bacteria | | strain | Biacore | 2-step-method |
|---|---|---|---|---|
| E. coli | BL21 (DE3) | B | + | + |
| | DH1 | K-12 | n.d. | + |
| | DH5α | K-12 | n.d. | + |
| | DH10b | K-12 | + | + |
| | GM2163 | K-12 | n.d. | + |
| | HB101 | K-12 | + | + |
| | Inv αF | K-12 | n.d. | + |
| | JM83 | K-12 | n.d. | + |
| | JM109 | K-12 | n.d. | + |
| | LE392 | K-12 | + | + |
| | NM522 | K-12 | n.d. | + |
| | sure | K-12 | + | + |
| | TG2 | K-12 | n.d. | + |
| | Top10 | K-12 | n.d. | + |
| | XL1-Blue | K-12 | n.d. | + |
| | D21 | | + | + |
| | D21e7 | | + | + |
| | D21e8 | | + | + |
| | D21f1 | | + | + |
| | W3110 | K-12 | + | n.d. |
| | DSM 613 | B | + | + |
| | DSM 5210 | K-12 | n.d. | + |
| | DSM 13127 | C | + | + |
| | MC 4100 | K-12 | + | + |

B

| bacteria | Biacore | 2-step-method |
|---|---|---|
| Citrobacter freundii | - | - |
| Enterobacter cloacae | n.d. | - |
| Klebsiella MK-1 | n.d. | - |
| Klebsiella 2668 | n.d. | (-) |
| Serratia marcescens | n.d. | - |
| Enterococcus faecalis | - | - |
| Kocuria rhizophila | - | - |
| Micrococcus luteus | - | unspecific |
| Proteus mirabilis | - | - |
| Pseudomonas aeruginosa | n.d. | - |
| Rathayibacter rathayi | - | - |
| Salmonella typhimurium | n.d. | - |
| Staphylococcus haemolyticus | n.d. | unspecific |

METHODS FOR PURIFICATION OF BACTERIAL CELLS AND COMPONENTS

This application claims priority to PCT/DE 02/02302, filed on Jun. 24, 2002, DE 101 29 815.3 filed Jun. 24, 2001. The entire content of these applications are hereby incorporated by reference.

The present invention relates to a method for the selective purification of bacterial cells and/or cell components wherein the purification is performed by means of a solid support.

The starting point of almost any further processing, analysis, or isolation of cell components is the enrichment of the cells, named cell harvest, usually being carried out by means of centrifugation. This centrifugation step is the main problem of the entire automation of methods, for example of the plasmid purification, since in addition to the high technical complexity for the integration of a centrifuge in a respective processing robot an extremely high precision of the start and stop position of the centrifugation process is required. Automatic methods of the further processing analysis or isolation of cell components usually starts with cells being enriched, centrifuged, or sedimented outside of the processing robot. For example, a nearly entire automation of the relevant methods is essential for a rapid analysis of complete genomes, proteoms, and also for a rapid determination of the structure and function in high throughput methods. The automation for example in the genome analysis has already been highly advanced: The bacterial growth as well as the plasmid isolation may be carried out automatically. However, an entire automation of the methods including the cell harvest is still not feasible. Particularly a selective cell harvest, that is the specific enrichment of particular cells out of a cell mixture, is not possible with the presently used methods.

The cell harvest is usually carried out with the following methods: The standard method of the cell harvest is the unspecific centrifugation of the bacterial cultures. A microplate centrifuge is necessary especially in those methods which are constructed for a higher throughput. However, the centrifugation as such is not suitable for an automation.

Though the filtration of the cultivated cells with respective filter membranes is feasible, that filtration also allows only an unspecific enrichment of the cells. In addition, the method is highly accident sensitive with respect to plugging in highly enriched cell suspensions and the high viscosity of the solutions as a consequence thereof.

The fluorescence activated cell sorting is a method in which a very thin liquid thread is used allowing the sorting and enrichment of single fluorescence labelled cells by means of the laser. By use of a respective fluorescence label, a certain specificity of the enrichment is possible, but due to the thin liquid thread, the method is limited to small volumes and thus to a low throughput. Therefore, only small cell amounts may be enriched, which is not sufficient for a further processing or an analysis of cell components. The high costs for the apparative equipment also prevent a strong propagation of the technique and slow down the simultaneous work necessary for a high throughput cell harvest.

The cells are bound directly to magnetic particles via ionic interactions and are locally concentrated by applying a magnetic field in case of the magnetic cell separation technique. Those methods for the unspecific concentration of bacterial cells have been distributed recently for the entire automation of the processing of plasmid or genomic DNA including the cell harvest by Chemagen (EP 1 118 676), Genpoint (WO 01/53525, WO 98/51693), Merck (WO 00/29562), as well as Promega (U.S. Pat. No. 6,284,470) or Amersham (WO 91/12079). However, these magnetic particles exhibit the drawback that on the one hand they bind the bacterial cells in an unspecific manner, and on the other hand they do not bind every bacterial species equally well. Due to the unspecificity of the binding, even different binding efficiencies in various strains of a species have been observed (Merck WO 00/29562).

Thus, one object of the present invention is the provision of a method which is feasible to selectively and fully automatically enriched bacterial cells and cell components and which may be incorporated into an automated analysis or isolation method. A further object of the present invention is the provision of solid supports for the selective enrichment of bacterial cells or cell components.

The object is achieved by the subject matter defined in the claims.

The following figures illustrate the invention.

FIG. 1 displays in a graphic the time dependency of the p12-dependent binding of $E.\ coli$ to magnetic beads. The values indicate the β-galactosidase activity of immobilised cells in relative units. VIK (rhombus symbols) stands for: two-step method (preincubation of cells and p12, subsequent binding to magnetic beads). VC (squares) stands for: one-step method (precoating of p12 to magnetic beads, subsequent immobilising of cells). −p12 (triangles) stands for: background (unspecific cell binding to beads without p12).

Figure 2:
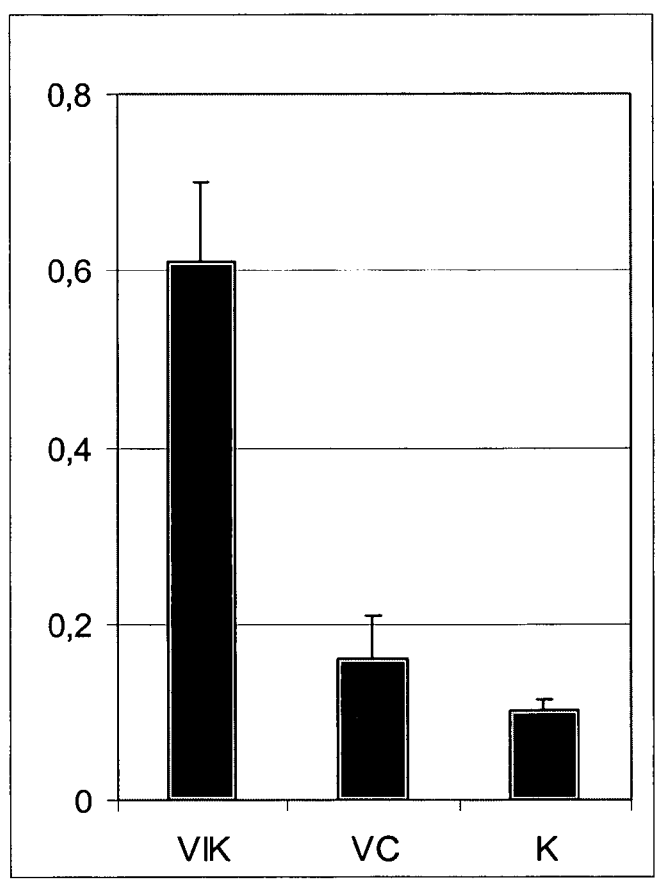

FIG. 2 displays in a graphic the binding of $E.\ coli$ to magnetic beads via the bacteriophage T4. The values indicate the β-galactosidase activity of immobilised cells in relative units. VIK stands for: two-step method (preincubation of cells and T4, subsequent binding to magnetic beads). VC stands for: one-step method (precoating of T4 to magnetic beads, subsequent immobilising of cells). K stands for: background (unspecific cell binding to beads without T4).

Figure 3:
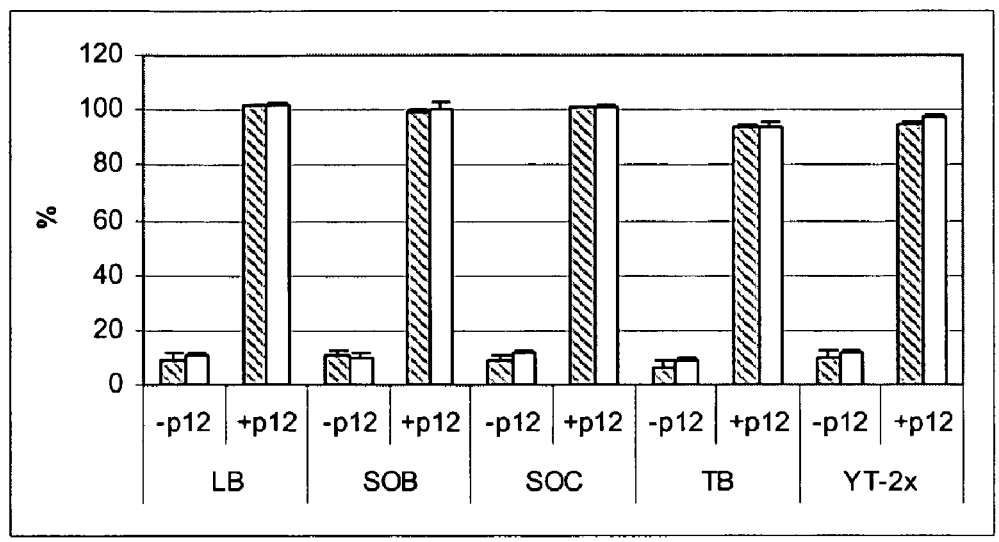

FIG. 3 displays in a graphic comparison the yield of $E.\ coli$ cells from different media. −p12 denotes the results without N-strep-p12. +p12 denotes the results with N-strep-p12. Hatched bars show the results with the strain $E.\ coli$ LE392, filled in bars denote the results with the strain $E.\ coli$ JM83. LB, SOB, SOC, TB, and YT 2× denote the respective media being used in the experiment. The values are shown as yield in % of the used cells, determined over the scattering of the supernatant at 600 nm after pelleting of the bound cells by means of a magnet.

Figure 4:
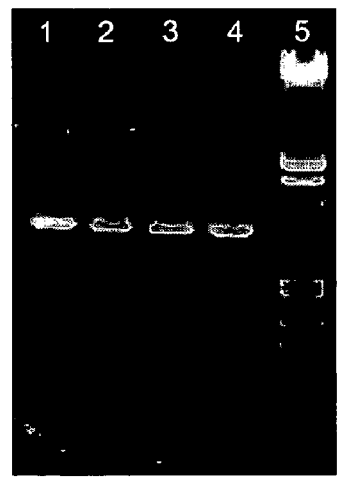

FIG. 4 shows graphically the result of the plasmid isolation after harvest of $E.\ coli$ with p12 according to the two-step method. Strain DH10b with plasmid pUC19. 1: centrifuged cells, DNA isolation via solid phase extraction, 2: cells harvested with the two-step method according to the present invention, DNA isolation via solid phase extraction, 3: centrifuged cells, DNA isolation via magnetic beads, 4: cells harvested with the two-step method according to the present invention, DNA isolation via magnetic beads, 5: standard.

FIG. 5 shows in a graphic display the enrichment of $E.\ coli$ cells from 10 ml culture volume, starting from a cell suspension of different cell densities ($10^9$-$10^7$ CFU/ml). Graph A: the filled in bars indicate the β-galactosidase activity of the cells bound via N-strep-p12, the hatched bars indicate the background without p12. Graph B: the filled in bars indicate the β-galactosidase activity of cells bound via T4-bio, the hatched bars indicate the background without T4.

Figure 6:
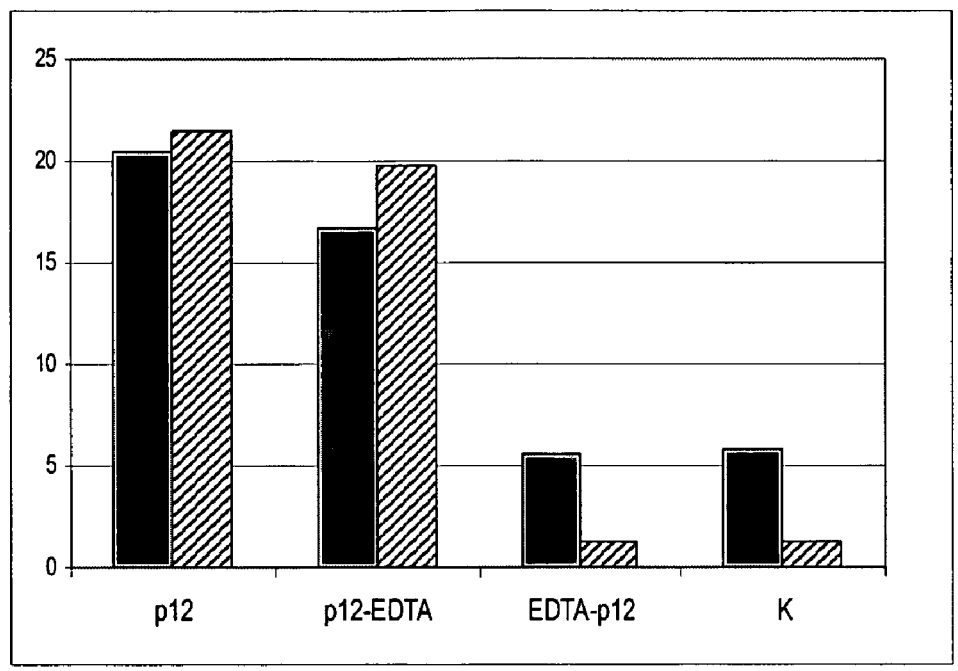

FIG. 6 shows schematically the harvest of living $E.\ coli$ via biotinylated p12 and streptavidin beads. The filled in bars indicate the scattering at 600 nm after two hours of growth. The hatched bars indicate the β-galactosidase activity of the cells. The abbreviations stand for: P12: the determinations of the cells immobilised to the beads, P12-EDTA: determinations of the cells stripped from the beads after the binding (supernatant after EDTA treatment), EDTA-p12: immobilising of the cells to the beads was prevented by the presence of EDTA; determinations of the unspecific cells to the beads, K: control experiment without p12; determinations at the beads.

FIG. 7 shows in a table the selective binding of p12 to bacterial cells. Table A lists the p12-dependent binding of different *E. coli* strains, table B shows the specificity of the p12-dependent binding. The abbreviation n.d. indicates not determined, + indicates the binding of p12 to the named bacteria, – indicates no binding of p12 to the cells.

Figure 8:
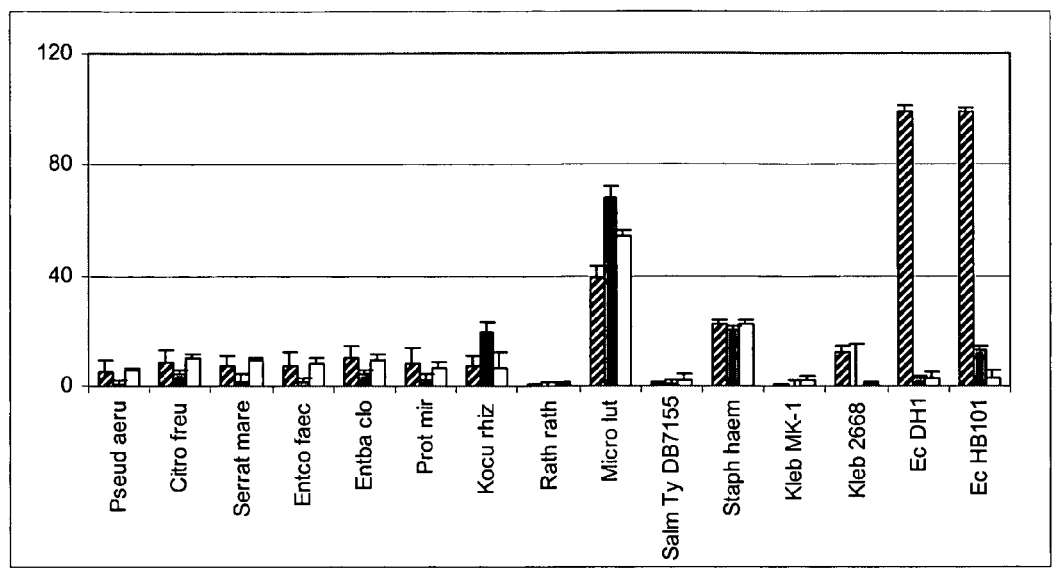

FIG. 8 shows graphically the specificity of the p12-dependent binding. The values indicate the yield of immobilised cells, determined over the scattering in the supernatant at 600 nm. The hatched bars indicate the values for the cell binding over N-strep-p12 (=specific binding). The dark filled in bars show the control without p12 (=unspecific adsorption). The light filled in bars indicate the values for the cell binding with p12, in the presence of 10 mM EDTA (=unspecific adsorption), however.

Figure 9:
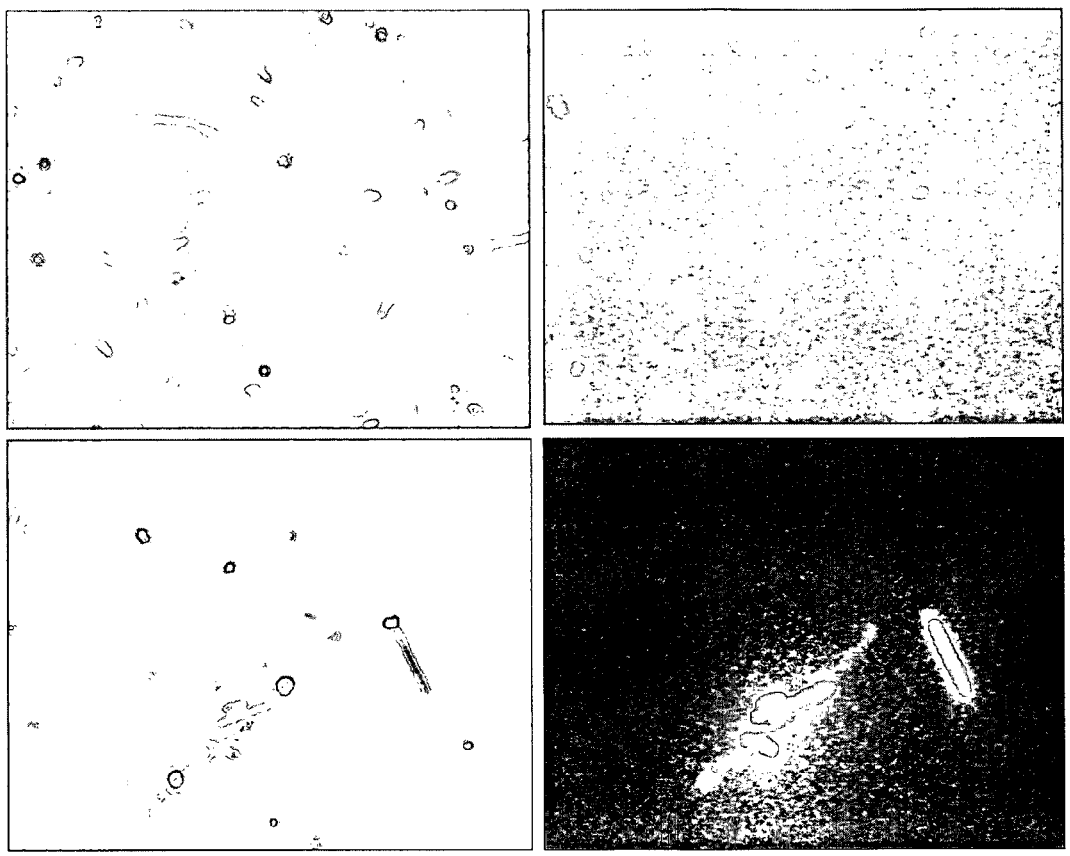

FIG. 9 shows images of light microscopy and fluorescence microscopy of the selective binding of *E. coli* to magnetic beads via T4-bio in a mixed culture of *E. coli* and *Serratia marcescens*. The *E. coli* cells were fluorescence labelled with FITC-labelled T4p12. The images on the left show exposures of light microscopy, the images on the right show exposures of fluorescence microscopy. The upper images show exposures of an experiment without T4-bio, the lower images show exposures of an experiment with T4-bio.

Figure 10:
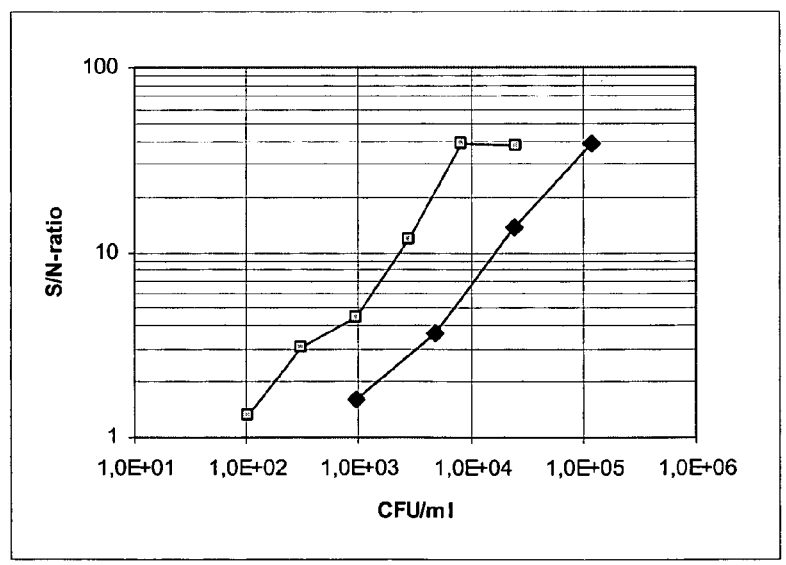

FIG. 10 shows graphically the result of the cell harvest after the two-step method with N-strep-p12 in solutions with various cell numbers. S/N-ratio indicates the signal to noise-ratio (signal with N-strep-p12 divided by the signal without N-strep-p12) of the p-galactosidase reaction of the bound *E. coli* cells, CFU/ml indicates the used cells (cell forming units) per ml. The squares indicate the results of the β-galactosidase activity of the measurement with a luminescent substrate. The rhombi indicate the results of the β-galactosidase activity of the measurement with a fluorescent substrate.

Figure 11:
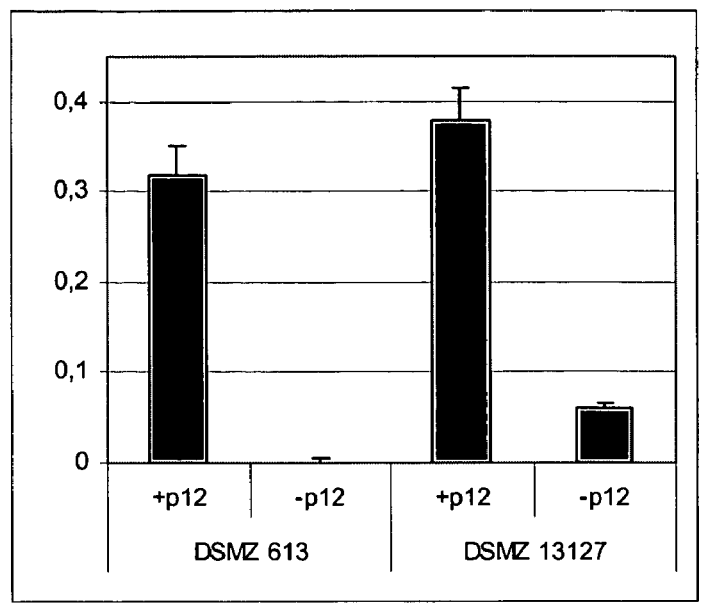

FIG. 11 shows graphically the result of the harvest of *E. coli* cells after the one-step method with T4p12 which is covalently bound to magnetic EM2-100/49 beads (Merck Eurolab). +p12 indicates the results with beads with T4p12, –p12 indicates the results with beads without T4p12, DSMZ 613 indicates the results with the strain *E. coli* DSMZ 613, DSMZ 13127 indicates the results with the strain *E. coli* DSMZ 13127.

Figure 12:
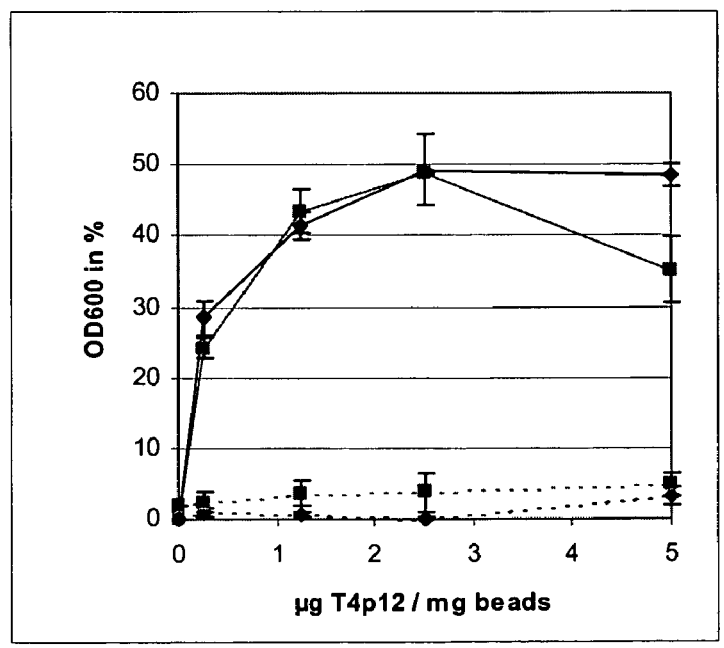

FIG. 12 shows graphically the results of the harvest of *E. coli* cells after the one-step method with T4p12 adsorbed to magnetic PVA-beads. The rhombi indicate the results with the beads PVA-011 (Chemagen), the squares indicate the results with the beads PVA-012. The continuous lines indicate the results with beads having adsorbed T4p12, dashed lines indicate beads without T4p12. The OD600 values indicate the %-values of harvested cells in % of the scattering of the supernatant after pelleting of the bound cells by means of a magnet.

The term "phage proteins" or "bacteriophage proteins", as used herein, refers to all bacteriophage proteins participating in the recognition and binding of the bacterial cells or the cell components. Said proteins my be localised depending on the morphological property of the phages, for example directly on the phage coat or on specific recognition structures, namely the tail fibres. Thus, the term "bacteriophage tail proteins" refers to phage proteins displaying the bacteriophage tail or being a part of the bacteriophage tail.

The term "specificity" as used herein means that the bacteriophages or phage proteins recognise and bind only a single genus or species, or a sub-species of bacterial cells or cell components, as well as that some bacteriophages or phage proteins recognise and bind specific bacteria groups.

The term "enrichment" or "purification" as used herein means the specific separation of bacterial cells or cell components from the aqueous solution, for example from the culture medium, in which the bacterial cells or cell components are located. The purification or enrichment is carried out by means of solid supports, for example magnetic particles, glass particles, agarose particles, reaction tubes, or microtiter plates.

One aspect of the present invention refers to the provision of methods for selective purification of bacterial cells or cell components, comprising the following steps: (two-step method)

a) contacting a sample containing bacterial cells or cell components with bacteriophages and/or bacteriophage proteins, preferably with an incubation time of about 3-5 minutes, b) subsequent incubation of said sample, containing the bacterial cells or cell components and the bacteriophages and/or bacteriophage proteins with a solid support, preferably for about 3-30 minutes, c) separation of the solid support with the bacterial cells or cell components bound via the bacteriophages and/or bacteriophage proteins to said solid support from the sample.

Bacterial cells or cell components may be enriched selectively with methods according to the present invention, for example from mixed cultures of different species or from a culture of a single species. Enriched cell components may be, for example, endotoxines, proteins, nucleic acids, or saccharides. The choice of appropriate bacteriophages and/or bacteriophage proteins allows the selectivity of the method. According to the method of the present invention, bacteriophages and/or bacteriophage proteins are most suited for a selective enrichment of bacteria or cell components, because phage-bacteria-systems have been evolved in nature for a long time so that the phages identify their host bacteria in a highly specific manner and with high binding affinity. Preferably bacteriophage proteins are used for the method of the present invention which are specific for the bacteria desired to be detected. Bacteriophages as well as bacteriophage proteins developed under adverse environmental conditions so that they are stable over influences, like temperature and pH-variations (Burda et al., Biological Chemistry 2000, 381, 255-258) et al., and thus may be used in the different purification buffers.

Which bacteriophages and/or bacteriophage proteins will be used depends on the fact which bacteria species are to be purified. For a following plasmid purification, those bacteriophages and/or bacteriophage proteins will be preferred which may bind the *E. coli* bacteria selectively, because they represent the commonly used bacteria for a plasmid preparation at present. A large number of known bacteriophages is available already for most of the bacteria described so far and may be utilised for a selective bacteria enrichment. The following table shows an overview of bacteria and their specific bacteriophages without being exhaustive. The phages and their respective host bacteria are commercially available from the following strain collections: ATCC (USA), DSMZ (Germany), UKNCC (Great Britain), NCCB (Netherlands), and MAFF (Japan). Moreover, bacteriophages directed against respective bacteria may be isolated for example from environmental samples according to standard methods, if required (Seeley, N. D. & Primrose, S. B., 1982, J. Appl. Bacteriol. 53, 1-17).

| Bacteria: | Phage |
|---|---|
| Acholeplasma: | 0c1r, 10tur, L2, L51, M1, MVG51, MV-L1, O1, SpV1, V1, V1, V2, V4, V5 |
| Actinomycetes: | 108/016, 119, 29, 37, 43, 51, 59.1, A1-Dat, Aeh2, Bir, M1, MSP8, ø115-A, ø150A, ø31C, P-a-1, PhiC, R1, R2, SK1, SV2, VP5 |
| Actinoplanes/Micromonospora: | Ap3, Ap4, Mm1, Mm3, Mm4, Mm5, phiUW 51 |
| Aeromonas: | 43, 44RR2.8t, 65, Aeh1 |
| Aeromonas hydrophila: | PM1 |
| Agrobacterium: | PIIBNV6, PS8, psi, PT11 |
| Alcaligenes: | 8764, A5/A6, A6 |
| Alteromonas: | PM2 |
| Amycolatopsis: | W11, W2, W4, W7 |
| Bacillus: | 1A, alpha, AP50, BLE, F, G, GA-1, II, IPy-1, mor1, MP13, MP15, ø105, ø29 (phi 29), øNS11, PBP1, PBS1, SP10, SP15, SP3, SP8, SPP1, SPβ, SPy-2, SST, type |
| Bacillus subtilis | 168, W23, SP50, W23, SP01 |
| Bdellovibrio: | MAC-1, MAC-2, MAC-4, MAC-5, MAC-7 |
| Brucella: | Tb |
| Caulobacter: | øCb12r, øCb2, øCb23r, øCb4, øCb5, øCb8r, øCb9, øCP18, øCP2, øCr14, øCr28 |
| Cellulomonas: | O11, O13, O2, O3, O5, O6, O8 |
| Chlamydia: | 1 |
| Chlamydia psittaci: | .phi.CPG1 |
| Clostridium: | Ceβ, F1, HM2, HM3, HM7 |
| Coryneforme | 7/26, A, A19, AN25S-1, Arp, AS-1, BL3, CONX, MT, N1, øA8010, S-6(L), β |
| Cyanobacteria: | A-4(L), AC-1, LPP-1, S-2L, S-4L, SM-1 |
| E. coli, (O157): | P1, T1, Tula, Tulb, Tull |
| E. coli: | 1ø3, 1ø7, 1ø9, 2D/13, Ae2, alpha10, alpha3, BE/1, BF23, dA, delta1, delta6, dø3, dø4, dø5, Ec9, eta8, f1, fd, G13, G14, G4, G6, HK022, HK97, HR, lambda, M13, M13mp18, M20, MM, MS2, Mu, O1, ø80, øA, øR, øX174, PA-2, P1, P1D, P2, P22, Qβ, R17, S13, St-1, T1, T2, T3, T4, T5, T6, T7, WA/1, WF/1, WW/1, zeta3, ZG/2, ZJ/2 |
| E. coli R1: | C21 |
| E. coli O8: | omega 8 |
| E. coli (K12): | U3 |
| Enterobacter: | chi, FC3-9, µ2, 01, 11F, 121, 1412, 3, 3T+, 50, 5845, 66F, 7480b, 8893, 9, 9266, a1, alpha15, b4, B6, B7, Beccles, BZ13, C-1, C16, C2, C-2, DdVI, Esc-7-11, f2, fcan, Fl, Folac, fr, GA, H, H-19J, I2-2, Ialpha, ID2, If1, If2, Ike, JP34, JP501, K19, KU1, M, M11, M12, MS2, NL95, ø92, øl, Øii, Omega8, pilHalpha, PR64FS, PRD1, PST, PTB, R, R17, R23, R34, sd, SF, SMB, SMP2, SP, β, ST, tau, tf-1, TH1, TW18, TW28, ViII, VK, W31, X, Y, ZG/1, ZIK/1, ZJ/1, ZL/3, ZS/3 |
| Klebsiella pneumoniae: | AP3, C3: |
| Lactobacillus: | 1b6, 223, fri, hv, hw222a, øFSW, PL-1, y5 |
| Lactococcus lactis: | 1, 643, c2, kh, ml3, P008, P127, 1358, 1483, 936, 949, BK5-T, c2, KSY1, P001, P008, P107, P335, PO34, PO87 |
| Leuconostoc: | pro2 |
| Listeria: | 4211, |
| Methanothermobacter: | psi M2 (ΨM2) |
| Micrococcus: | N1, N5 |
| Mollicutes: | Br1, C3, L3 |
| Mycobacterium: | I3, lacticola, Leo, ø17, R1-Myb |
| Nocardia/Rhodococcus/Gordona: | N13, N18, N24, N26, N36, N4, N5 |
| Nocardioides: | X1, X10, X24, X3, X5, X6, D3, D4, |
| Pasteurella: | 22, 32, AU, C-2 |
| Promicromonospora: | P1, P2, P3, P4 |
| Pseudomonas aeruginosa: | Phi CT, phi CTX, PB-1 |
| Pseudomonas: | 12S, 7s, D3, F116, gh-1, gh-1, Kf1, M6, ø1, øKZ, øW-14, Pf1, |
| Pseudonocardia: | W3 |
| Rhizobium: | 2, 16-2-12, 2, 317, 5, 7-7-7, CM1, CT4, m, NM1, NT2, ø2037/1, ø2042, øgal-1-R, WT1 |
| Saccharomonospora: | Mp1, MP2 |

-continued

| Bacteria: | Phage |
|---|---|
| Saccharothrix: | W1 |
| Salmonella: | epsilon15, Felix 01, 16-19, 7-11, H-19J, Jersey, N4, SasL1, ViI, ZG/3A, San21 |
| Salmonella typhimurium: | A3, A4, P22 |
| Spiroplasma: | 4, C1/TS2 |
| Sporichthya: | Sp1 |
| Staphylococcus: | 107, 187, 2848A, 3A, 44AHJD, 6, 77, B11-M15, Twort |
| Streptococcus: | 182, 2BV, A25, A25-24, A25-omega8, A25-PE1, A25-VD13, CP-1, Cvir, H39 |
| Streptomyces: | P23, P26, phi A. streptomycini III, phi8238, phiC31, S1, S2, S3, S4, S6, S7, SH10 |
| Terrabacter: | Tb1, Tb2 |
| Tsukamurella: | Ts1 |
| Vibrio: | 06N-22P, 06N-58P, 06N-58P, 4996, alpha3alpha, I, II, III, IV, kappa, nt-1, OXN-100P, OXN-52P, v6, Vfl2, Vf33, VP1, VP11, VP3, VP5, X29 |
| Xanthomonas: | Cf, Cf1t, RR66, |
| Yersinia: | 8/C239, phiYeO3-12, YerA41 |

If single phage proteins instead of bacteriophages are used, there is an advantage because in this case the properties of a single protein instead of a complex of proteins and nucleic acids may be used. Phage proteins are very stable (Burda et al., Biological Chemistry 2000. 381, 255-258); the stability of a single protein is much easier to control than the stability of a protein complex. In comparison to complete phages, it is important that they are easier to modify (genetically, but also chemically), for example the introduction of tags. Moreover, the use of phage proteins is an advantage in specific connecting methods, i.e. the isolation of nucleic acids (plasmid DNA, RNA, genomic DNA), because compared to the use of complete phages no nucleic acid contamination is possible.

Preferred are phage tail proteins from the family of myoviridae, of podoviridae, and siphoviridae, particularly short phage tail proteins, particularly the short phage tail proteins of the even-numbered T-phages, for example T4, T2, or K3, particularly the bacteriophage tail proteins p12 from T4, p12 from T2 (GenBank Accession Number X56555), p12 from K3 (cf. Burda et al., 2000, Biol. Chem., Vol. 381, pp. 255-258) or the bacteriophage tail proteins from the phages Felix 01, P1, or PB1. As an example, the short bacteriophage tail proteins of the phagesT4 (p12) and from P1 bind to coliformes, the short phage tail protein from Felix 01 binds to salmonellas, and the short phage tail protein from PB1 binds to pseudomonas.

Phage tail proteins like p12 or P22 tailspike protein display a high stability over proteases, detergents, chaotropic agents, for example urea or guanidinium hydrochloride, or higher temperatures (Goldenberg, D. und King, J.; Temperature-sensitive mutants blocked in the folding or subunit assembly of the bacteriophage P22 tail spike protein. II. Active mutant proteins matured at 30° C., 1981, J. Mol. Biol. 145, 633-651. Miller, S., Schuler, B. und Seckler, R.; Phage P22 tailspike: Removal of headbinding domain unmasks effects of folding mutations on native-state thermal stability, 1998, Prot. Sci. 7, 2223-2232; Miller, S., Schuler, B. und Seckler, R.; A reversibly unfolding fragment of P22 tailspike protein with native structure: The isolated β-helix domain, 1998, Biochemistry 37, 9160-9168; Burda et al., 2000, Biol. Chem., Vol. 381, pp. 255-258). The removal of the phage head and phage base plate binding region, respectively, of these proteins may reduce a potentially existing aggregation sensitivity. Interestingly, the single domains and subunits, respectively, of these proteins are significantly less stable than the intact or only marginally reduced trimers (Miller et al., Prot. Sci. 1998; 7: 2223-2232. Phage P22 tailspike protein: Removal of head-binding domain unmasks effects of folding mutations on native-state thermal stability; Miller-S, et al., Biochemistry 1998; 37: 9160-9168. A reversibly unfolding fragment of P22 tailspike protein with native structure: The isolated β-helix domain). Furthermore the single domains and subunits, respectively, are presumably hardly stable and functionally expressable: phage tail proteins and virus receptor proteins are often available as intensely drilled trimers, which has been shown in crystallographic experiments wherein the C-terminus may fold back, which is a mechanism possibly providing an additional protection against proteases (Mitraki A, Miller S, van Raaij M J. Review: conformation and folding of novel Beta-structural elements in viral fibre proteins: the triple Beta-spiral and triple Beta-helix. J Struct Biol. 2002 137(1-2):236-247), Moreover, these proteins exist in the native condition as homotrimers. The trimers contribute with three binding sites to a stronger binding of bacteria by an increase of the avidity.

With the even-numbered T-phages (T4, T2, K3) as an example, the binding mechanism of the bacteriophage proteins to the single bacteria should be clarified. In this genus, there are two components on the host side which are recognised by the phages: firstly a surface protein specific for individual phages, secondly the lipopolysaccharide (LPS) which is possessed by all gram-negative bacteria in a modified form on their outside and is orientated to the environment. The long tail fibres of the even-numbered T-phages play a role in the specific recognition of the host bacteria, whereas the LPS serves as a receptor for the short tail fibres. It is known from the phage T4 from *E. coli* that the specific interaction with the host bacterium mediated by the long tail fibres will become irreversible as soon as the short tail fibres have been bound to the bacteria surface. The short tail fibre is not responsible for the correct specificity within the host bacteria genus and therefore may be replaced between the different even-numbered T-phages.

Bacteriophage tail proteins may easily be recombinantly produced in large numbers and may be purified using appropriate tags or simple chromatographic standard separation methods. Phages as well as host strains are largely commercially available via strain collections or may be isolated by simple means. In the method of the present invention, however, not only the naturally occurring bacteriophage tail proteins may be used, but also their variants. The variants as used in the present invention means that the bacteriophage tail proteins exhibit an altered amino acid sequence. Said variants may be obtained by screening of the naturally occurring variants or by random mutagenesis or targeted mutagenesis, but also by chemical modification. The bacteriophage tail proteins used in the method of the present invention may be adapted by a targeted or random mutagenesis in their host specificity and their binding behaviours, respectively, to the support structures. By means of the mutagenesis, mutations are introduced which may be amino acid additions, deletions, substitutions, or chemical modifications. These mutations produce an alteration of the amino acid sequence in the binding region of the phages or phage proteins, with the intention to adapt the specificity and binding affinity to the experimental requirements, for example to enhance the binding of the bacteria to the isolated phage proteins or to make their binding irreversible, to enhance the washing options. Moreover, a genetic or biochemical modification of the phage proteins may be performed with the intention optionally to switch off the present enzymatic activity to improve the binding or make the binding irreversible.

For binding purposes of the bacteria and/or cell components to be purified to the bacteriophages and/or bacteriophage tail proteins in the two-step method, the sample, for example an overnight culture, is contacted with the bacteriophages and/or bacteriophage tail proteins and is preferably incubated. The incubation occurs at a temperature in the range of 4° C. to 90° C., preferably at a temperature in the range of 4° C. to 45° C., more preferred at a temperature in the range of 15° C. to 37° C., furthermore preferred at a temperature in the range of 20° C. to 37° C., in particular at RT, for up to 6 hours, preferably up to 4 hours, more preferred 2 hours, in particular 1 hour, in particular preferred 1-20 minutes, exceptionally preferred 3-5 minutes. For example, the incubation can occur for 2 to 120 minutes at 4° C. to 37° C., preferably for 20 to 30 minutes at 25° C. to 37° C., preferably more preferred for 3-5 minutes at 37° C.

The sample is contacted with solid supports subsequently and incubated. Solid supports may be, for instance, magnetic particles (paramagnetic or ferromagnetic), glass particles, agarose particles, luminex particles, reactions tubes, or microtiter plates.

In case of using magnetic particles, they were subsequently added to the sample. The magnetic particles bind the bacteriophage/bacteriophage protein-bacteria/cell component complex, which is then easily separated from the sample by using magnetic means, and which may then be purified. The magnetic means may be positioned at the outside of the container and either may be switched on for the enrichment so that the magnetic particles are collected at the container wall, or may slide along the outside wall of the container so that the magnetic particles are collected e.g. at the bottom of the container. The enrichment with a permanent magnet is preferred. The magnetic means may also immerse into the container and the sample so that the magnetic particles deposit at the magnetic means (the magnetic means may be covered by a pipette tip or a comparable disposable). In comparison to centrifugation or filtration techniques, the bacteria are subject to only minimal shear rates and therefore may be enriched with high yield in an active/living manner, if required. The easy handling facilitates easy and fast buffer/solution changes and may both easily be performed on a large scale, and well automated.

The magnetic particles exhibit a diameter allowing the binding of a sufficient amount of cells or cell components per particle. Preferably the magnetic particles exhibit a diameter in the range of about 0.5 to about 4 µm, in particular in the range of about 0.5 to about 2 µm, more preferred in the range of about 0.8 to about 1.8 µm, most preferred about 1 µm.

The binding of the bacteriophage/bacteriophage protein-bacteria/cell component complexes to the solid supports, for example magnetic particles, preferably occurs via appropriate coupling groups, in particular polypeptides and/or low molecular substances. These polypeptides may also be antibodies, lectins, receptors or anticalins specific for the bacteriophages and/or bacteriophage proteins. Furthermore, the bacteriophages and/or bacteriophage proteins may be coupled to low molecular substances, e.g. biotin, to bind to polypeptides, e.g. streptavidin, via these low molecular substances wherein the polypeptides may be immobilised to the support. Instead of biotin, the so-called strep-tag (Skerra, A. & Schmidt, T. G. M. Biomolecular Engineering 16 (1999), 79-86) may be used, which is a short amino acid sequence and binds to Streptavidin. Furthermore, the his-tag may be used, which may bind to a support material via bivalent ions (zinc or nickel) or an antibody which is specific for the his-tag (Qiagen GmbH Hilden, Germany). The strep-tag as well as the his-tag are preferably bound by means of DNA recombination technology to the recombinantly produced bacteriophage proteins. This coupling may occur in a directed manner, e.g. to the N- or C-terminus. Since particularly in the two-step method a high binding constant is essential for an effective enrichment, the coupling combination of biotin/streptavidin with a kD of ~$10^{-15}$ M (Gonzales et al. J. Biol. Chem., 1997, 272 (17), pp. 11288-11294) is preferred in particular. It was shown that this non-covalent binding combination works better than the available antibodies, anticalins, receptors and lectins.

For a binding of the complex the magnetic particles are contacted with the bacteriophage/bacteriophage protein-bacteria/cell component complex and are preferably incubated. The incubation occurs at a temperature in the range of 4° C. to 90° C., particularly in the range of 4° C. to 45° C., more preferred at a temperature in the range of 15° C. to 37° C., particularly preferred at a temperature in the range of 20° C. to 37° C., in particular at RT, for up to 6 hours, preferably up to 4 hours, more preferred 2 hours, in particular 1 hour, in particular preferred 1-20 minutes, exceptionally preferred 3-5 minutes. For example, the incubation can occur for 2 to 120 minutes at 4° C. to 37° C., preferably for 20 to 30 minutes at 25° C. to 37° C., preferably more preferred for 3-5 minutes at 37° C.

The method of the present invention is performed with other solid supports which may be added to the sample in the analogous manner. The single incubation conditions and separation steps have to be adapted for the different solid supports accordingly. This may easily be performed in test series and does not require any further explanation for the skilled artisan.

Alternatively, the two-step method may be performed in accordingly coated solid supports which may not be added to the sample, but wherein the sample is added onto or into the solid support, e.g. a microtiter plate or a reaction tube. For this purpose, the sample is added after step a), e.g. into the respective wells of the microtiter plate, and is incubated there, particularly for about 20-30 minutes with the other conditions remaining as described above. The wells of the microtiter plate or the inner walls of a reaction tube may exhibit the same coatings as described above for the magnetic particles.

The enrichment and purification, respectively, of the bacterial cells and/or cell components may also be performed in a method comprising the following steps (one-step method):
a) contacting a sample containing bacterial cells and/or cell components with a magnetic support on the surface of which bacteriophages and/or bacteriophage proteins are applied, preferably with an incubation of about 3-60 minutes,
b) separating the magnetic support with the bacterial cells and/or cell components bound to it from the sample.

The methods according to the present invention (one-step and two-step method) may be used, for example, as an alternative for centrifugation and thus for the first time allows the automated purification of bacterial cells. This for the first time enables the automation of, e.g., the genome analysis, i.e. from the inoculation of the bacterial cultures to the determination of the sequence. Furthermore, the method of the present invention may be used, for example, to isolate cell components, particularly of lipopolysaccharides, endotoxines or exopolysaccharides.

The following embodiments of the coupling or immobilisation of bacteriophages and/or bacteriophage proteins to the magnetic particles (one-step method) apply accordingly to the coupling or immobilisation of bacteriophages and/or bacteriophage proteins and polypeptides to the solid supports (two-step method). The coating of the solid supports with the previously described polypeptides or the bacteriophages and/or bacteriophage proteins may occur in a different manner.

The bacteriophages and/or bacteriophage proteins may be fixed to the solid supports via covalent coupling. This allows a very tight binding to the support and thus the application of severe washing conditions for the washing of the cells which is possibly required for a further processing of the enriched cells. The coupling of the bacteriophages and/or bacteriophage proteins via adsorption is a very simple and cost-effective method. One-step as well as two-step methods are possible by means of coupling the bacteriophages and/or bacteriophage proteins via biotin/streptavidin or comparable ligand/receptor systems. The streptavidin used in this approach may be fixed via adsorption, as well as via chemical coupling. A functional immobilisation is important in the coating method, that means that despite their binding to the solid supports, the bacteriophages and/or bacteriophage proteins exhibit structures which are accessible to bacteria.

The bacteriophages and/or bacteriophage proteins may be coupled via covalent coupling to support materials which have already been activated by the manufacturers, for instance to magnetic particles by Merck, Estapor® (microspheres), etc. via standard conditions, for example —$NH_2$ via cyanuryl chloride (Russina Chemical Rev., 1964, 33: 92-103), or —COO— via EDC (1-Ethyl-3'[3' Dimethylaminopropyl]carbodiimide) (Anal. Biochem. 1990, 185: 131-135). Moreover, the solid supports may be activated directedly using appropriate methods. Furthermore, the coupling may occur via maleimide or iodoacetyl spacer to, for instance, a N-terminal introduced cysteine.

The immobilisation of the bacteriophages and/or bacteriophage proteins to the support material via adsorption may be performed by incubation of a bacteriophage and/or bacteriophage protein solution in aqueous buffer, for instance 100 mM Tris pH 7.3, or 100 mM sodium phosphate pH 7.5, PBS (10 mM sodium phosphate pH 7.4, 150 mM sodium chloride) for several hours or overnight at 4° C. to 45° C., preferably at 15° C. to 37° C., more preferred at 20° C. to 37° C., in particular preferred at 37° C. or RT, in particular preferred at 30° C. to 65° C. for 2-4 hours. The coating solution is discarded after the adsorption and the support structure is stored in aqueous, optionally in buffered solution.

A further aspect of the present invention is a solid support, in particular a magnetic particle or a microtiter plate, either coated with bacteriophages and/or bacteriophage proteins, or coated with polypeptides directed against bacteriophages and/or bacteriophage proteins. These polypeptides may be antibodies, lectins, receptors or anticalins specific for the bacteriophages and/or bacteriophage proteins. The solid supports may be coated furthermore with streptavidin.

A further aspect of the present invention are bacteriophage proteins coupled with so-called tags, for example the strep- or the his-tag, particularly to the 3'- or 5' terminus, more preferred to the 5' terminus. The coupling or linking of the tags with the bacteriophage proteins via DNA recombination technology is preferred. The production of the nucleic acid, comprising the sequence of the bacteriophage protein and the tag, and the production of the expression product are state of the art and there is no need to explain the production in detail at this point. A further aspect of the present invention is the nucleic acid sequence coding the bacteriophage protein together with the strep- or the his-tag. A p12 protein from the bacteriophage T4 is a particularly preferred bacteriophage protein modified with the strep- or the his-tag, however, all other bacteriophage proteins of the listed bacteriophages from the above table are also preferred.

A further aspect of the present invention are bacteriophage proteins with a tag exhibiting a surface-exposed cysteine for the specific, directed biotinylation, e.g. the tags according to SEQ ID NOs: 5, 6 or 7. One example for a p12 with a tag is the amino acid sequence depicted in SEQ ID NO: 8. Preferred is a p12 with a tag, in particular with a tag with a surface-exposed cysteine, in particular a p12 with a tag according to SEQ ID NOs: 6 and 7. In addition, said directed biotinylation may be mediated by an appropriate spacer or linker. Furthermore, the present invention relates to the amino acid sequences according to SEQ ID NOs: 5, 6 and 7. Furthermore, the present invention relates to nucleic acids coding for the amino acid sequences according to SEQ ID NOs: 5, 6 and 7.

A further aspect of the present invention relates to a kit for the enrichment of bacterial cells and/or cell components, comprising the solid supports according to the present invention, for example the magnetic particles, glass particles, agarose particles, reaction tubes or microtiter plates as well as the solutions including the test reagents necessary for the enrichment of the bacteria and/or cell components.

The kit for the enrichment with magnetic particles includes in particular a stabilised solution of a p12-variant with a cysteine residue for the directed biotinylation introduced at the N-terminus, for example NS-T4p12 (or T4p12bio) 1 mg/ml in 100 mM TrisHCl pH8, 150 mM NaCl, 1 mM EDTA, 0.05% Tween 20, supplement with a protease inhibitor mixture (Sigma) as a solution (preferred storage at 4° C.) or as a lyophilisate. Furthermore, the kit includes a particle solution consisting of streptavidin- or streptactin-coated magnetic particles in a stabilising solution (PBST with sodium azide 0.005%).

The kit for an enrichment with microtiter plates includes in particular a stabilised solution of a p12-variant with a cysteine residue for the directed biotinylation at the N-terminus, for example NS-T4p12 (or T4p12bio) 1 mg/ml in 100 mM TrisHCl pH8, 150 mM NaCl, 1 mM EDTA, 0.05% Tween 20, supplement with a protease inhibitor mixture (Sigma) as a solution (preferred storage at 4° C.) or as a lyophilisate. The kit furthermore includes a streptavidin- or streptactin-coated microtiter plate.

The following examples illustrate the invention and are not to be understood as limiting. If not indicated otherwise, molecular biological standard methods have been used, as for example described by Sambrook et al., 1989, Molecular cloning: A Laboratory Manual 2. Edition, Cold Spring Harbor Laboratory Press, Cold Spring Harbor, N.Y.

1. The purification of wild type T4 p12 was carried out according to the method described in Burda, M. R. & Miller, S. Eur. J. Biochem. 1999, 265 (2), 771-778.

2. Construction of p12 with a N-terminal strep-tag (N-strep-p12):

The nucleotide sequence of the strep-tag (U.S. Pat. No. 5,506, 121) was introduced to the 5' terminus of the T4p12 gene via PCR. For the 5' terminus of the p12 gene a primer was constructed (5'-GAA GGA ACT AGT CATATG GCT AGC TGG AGC CAC CCG CAG TTC GAA AAA GGC GCC AGT AAT AAT ACA TAT CAA CAC GTT-3'), (SEQ ID NO:1) including the nucleotide sequence of the strep-tag at its 5' terminus (printed in italics in the sequence) and having a restriction recognition sequence (NdeI, underlined in the sequence) in such a manner that the gene may be inserted in the correct reading frame into the expression plasmid. A primer was constructed was constructed for the 3' terminus of the p12 gene introducing a BamH1 restriction recognition sequence (printed in italics in the sequence) behind the p12 gene (5'-ACG CGC AAA GCT TGT CGA CGG ATC CTA TCA TTC TTT TAC CTT AAT TAT GTA GTT-3'), (SEQ ID NO:2). The PCR was performed with 40 cycles (1 min 95° C., 1 min 45° C., and 1 min 72° C.). The PCR preparation was cleaved with the restriction endonucleases NdeI and BamH1 and the desired fragment was inserted in the NdeI and BamH1 site of the expression plasmid pET21a (Novagen, Merck Eurolab, Darmstadt, DE) after size directed separation via an agarose gel and elution from the gel. The sequence of the N-strep-p12 gene was verified by DNA sequencing. The further steps to the plasmid pNS-T4p12p57 were performed as described by Burda, M. R. & Miller, S. (Eur. J. Biochem. 1999, 265 (2), 771-778). The plasmid pNS-T4p12p57 was then transformed into the expression strain BL21 (DE3) (Novagen, Merck Eurolab, Darmstadt, DE).

3. Introduction of a N-terminal cysteine residue in N-strep-p12 (N-strep-S3C-p12 and N-strep-S14C-p12):

The introduction of a N-terminal cysteine residue (bold type) was performed as described under 2. above with two new primers for the 5' terminus being constructed. The primer 5'-GM GGA ACT AGT CATATG GCT TGT TGG AGC CAC CCG CAG TTC GAA AAA GGC GCC AGT AAT AAT ACA TAT CAA CAC GTT-3' (SEQ ID NO:3) was used for the N-strep-S3C-p12, and the primer 5'-GM GGA ACT AGT CATATG GCT AGC TGG AGC CAC CCG CAG TTC GAA AAA GGC GCC TGT AAT AAT ACA TAT CM CAC GTT-3' (SEQ ID NO:4) was used for the N-strep S14C-p12.

4. Purification of N-strep-p12 protein:

The E. coli strain BL21 (DE3) with the plasmid pNS-T4p12p57 was cultured in 2 l shaking cultures (LB medium with ampicillin 100 µg/ml) up to an OD600 of 0.5-0.7 at 37° C. and the expression of the N-strep-p12 protein was induced by adding 1 mM IPTG (Isopropyl-1-thiogalactopyranoside). The cells were harvested after incubation at 37° C. for 4 hours. Harvested cells from a 10 l culture were resuspended in 50 ml sodium phosphate, 20 mM pH 7.2, 2 mM MgSO$_4$, 0.1 M NaCl, broken up by a triple French press treatment (20,000 psi), and were subsequently centrifuged for 30 minutes at 15,000 rpm (SS34). After washing it twice in the same buffer, the N-strep-p12 protein was extracted from the pellet by stirring for 30 minutes in 40 mM TrisHCl pH 8.0, 10 mM EDTA. The preparation was centrifuged for 30 minutes at 15,000 rpm (SS34) and the supernatant with the separated NS-p12 was stored at 4° C. The extraction was repeated twice and the combined supernatants were applied to a streptactin-affinity column (15 ml) equilibrated with buffer "W" (100 mM TrisHCl pH 8, 1 mM EDTA, 150 mM NaCl) (IBA GmbH, Göttingen, DE). After washing with 5 volumes of the column with buffer "W", the column was eluted with 3 volumes of buffer "W" with 2.5 mM desthiobiotin in buffer "W". After repeated dialysis with "W" and concentration, the concentration and purity of N-strep-T4p12 was determined via SDS-PAGE and UV Spectroscopy (Burda et al. 1999). In this way, about 100 mg N-strep-T4p12 were purified from a 10 l culture.

| Name | Sequence of the tag | |
|---|---|---|
| Nstrep-p12 | MASWSHPQFEKGAS | SEQ ID NO:5 |
| Nstrep-p12-S3C | MACWSHPQFEKGAS | SEQ ID NO:6 |
| Nstrep-p12-S14C | MASWSHPQFEKGAC | SEQ ID NO:7 |

5. Alternative purification of p12:

The cell pellet (from a 10 l culture, BL21 (DE3), transformed with the plasmid pNS-T4p12p57 or pT4p12p57) was resuspended in buffer 1 (10 mM sodium phosphate pH 9, 500 mM NaCl, 4 mM $MgCl_2$) and broken up via French press (as described under 3.). Subsequently the material was centrifuged at 20,000 rpm (SS34) for 45 minutes and the pellet was resuspended (i.e. washed) in about 25 ml of buffer 1. This washing step was repeated twice and the pellet was extracted with 25 ml of buffer 2: (50 mM NaPi pH 5,100 mM NaCl, 25 mM EDTA). The resuspended pellet was stirred for the extraction for 60 minutes at RT and afterwards centrifuged (20,000 rpm (SS34) for 45 minutes). Said extraction was repeated twice if required. Afterwards, the supernatants of the extraction were combined and applied directly to an anion exchange column (ResoureceS, Pharmacia). 15 mM sodium hydrogen phosphate, 15 mM sodium formate, 30 mM sodium acetate, pH 5.0, 50 mM NaCl were used as a running buffer. The elution occurred via a linear salt gradient of 50 mM NaCl to 60 mM NaCl in the running buffer. The purified p12 was subsequently dialysed for storage against 50 mM Tris pH 8.5, 150 mM NaCl, 5 mM EDTA or PBS, frozen in aliquots in $N_2$, and stored at −20° C.

6. Biotinylation of p12:

For the biotinylation of the p12 protein, either EZ-Link™Sulfo-NHS-LC-LC-Biotin or EZ-Link™TFP-PEO-Biotin (biotin labeling reagents) by Pierce, USA, was used or the biotinylation was performed according to the methods of the manufacturer. About 30 molecules of biotin per p12-trimer were used for the biotinylation. The coupling of biotin was subsequently verified with a HABA-assay (Savage M D, Mattson G, Desai S, Nielander G W, Morgensen S, and Conklin E J, 1992, Avidin-Biotin Chemistry: A Handbook, Pierce, Ill.) and quantified. Finally, an average of 5-10 molecules of biotin per p12-trimer were bound.

7. For the biotinylation of the N-terminal introduced cysteine, EZ-Lin™PEO-Maleiimid-Biotin and EZ-Link™TPEO-liodoacetyl-Biotin by Pierce, USA, were used according to the instructions of the manufacturer. The reaction was verified as described under 5. above.

8. Biotinylation of the bacteriophage T4:

The bacteriophage was purified according Bachrach U and Friedmann A (1971) Practical procedures for the purification of bacterial viruses, Appl. Microbiol. 22: 706-715. The purified phage was dialysed against PBS and labelled with EZ-Link™Sulfo-NHS-LC-LC-Biotin or EZ-Link™TFP-PEO-Biotin by Pierce, USA, according to the instructions of the manufacturer in a ratio of 100-100,000 biotin molecules per phage.

9. p12-dependent harvest of E. coli according to the one-step method and the two-step method (FIG. 1):

In the binding step according to the one-step method (VC) the N-strep-p12 protein was incubated for 1 hour with the magnetic streptavidin beads (10 μg protein/50 μl 1% beads) and the beads were subsequently washed three times with PBST. For the cell binding step, 200 μl of an E. coli overnight culture diluted 1 to 10 in LB (about $1×10^8$ cells/ml) per well in a microtiter plate were mixed with 10 μl of the N-strep-p12 coated beads and incubated for different periods of time at RT (FIG. 1). The beads were concentrated subsequently with the bound cells via a magnetic separator (Bilatec AG, Mannheim, DE) for 3-5 minutes at the walls of the wells. The beads were washed three times with PBST and the β-galactosidase activity (Apte S C et al., 1995, Water res. 29, 1803-06) of the cells attached to the beads were determined subsequently. For the binding step according to the two-step method, a 1 to 10 dilution of an E. coli overnight culture (about $1×10^8$ cells/ml) were incubated for 1 hour (in further approaches for 1 minute, 3 minutes, 10 minutes, 30 minutes) with the N-strep-p12 protein (10 μg protein/ml cell suspension) at RT. Subsequently, 200 μl of the protein-cell-mixture were added to 10 μl of 1% magnetic streptavidin beads and incubated at RT for the times given in FIG. 1. The determination of the bound cells was performed according to the one-step method.

10. T4-dependent binding of E. coli according to the one-step method (VC) and the two-step method (VIK) (FIG. 2)

In the binding step according to the one-step method (VC), the biotinylated phage T4 (100 biotin molecules/phage) were bound for 1 hour to 1% streptavidin beads ($10^{10}$ PFU/ml 1% beads) and the beads were washed three times with PBST subsequently. After 2 hours of the cell binding step (25 μl phage beads/ml cell suspension), the beads were washed and the bound E. coli were determined via the β-galactosidase activity (the data are given in relative units). In the binding step according to the two-step method (VIK), the cells were incubated with the biotinylated phages for 1 hour ($2.5×10^8$ PFU/ml cell suspension) and the mixture was incubated subsequently for 2 hours with the streptavidin beads (25 μl 1% beads/ml cell suspension). The further steps were performed according to the one-step method. During the continuous incubation of phage and bacteria, the antibiotics Rifampicin (25 μg/ml), Chloramphenicol (25 μg/ml) and Tetracycline (2 μg/ml) were added to the medium.

11. Harvest of E. coli cells according to the two-step method from different growth media (FIG. 3):

The E. coli strains LE392 and JM83 were grown overnight in the respective media. N-strep-p12 (10 μg/ml cell suspension) were added to 200 μl of cell suspension. 10 μl 1% streptavidin beads were added after 5 minutes of incubation at RT, mixed by pulling it three times with a pipette, and were incubated a further 5 minutes at RT. Subsequently, the bacteria beads complexes were removed by means of the above described magnetic separator for 3-5 minutes and the cells remaining in the supernatant were determined via the scattering of the supernatant at 600 nm.

12. Plasmid isolation of E. coli after cell harvest via the two-step method (FIG. 4).

300 μl each of a E. coli overnight culture containing the plasmid pUC19 were harvested according to the two-step method as described under example 9. After removal of the cells by means of the above described magnetic separator, the plasmid was isolated from the cells in a first method via the solid phase extraction methods (QIAprep® (chromatographic material), Qiagen, Hilden, DE) and also via a method using magnetic beads (Bilatec, Mannheim, DE) according to the instructions of the manufacturers.

13. Enrichment of E. coli cells from 10 ml culture volume via N-strep-p12 and via the biotinylated bacteriophage T4-bio according to the two-step method (FIG. 5):

For the enrichment with N-strep-p12, 10 ml of E. coli cultures with $10^9$, $10^8$ and $10^7$ cells per ml were mixed with 30 μg and 6 μg protein each, respectively, and scrolled for 1 hour at 37° C. For the enrichment with T4-bio, 10 ml cultures with $10^9$, $10^8$ and $10^7$ cells per ml were each added to $10^{10}$ T4-bio phages and 10 μg Rifampicin/ml and 2 μg Tetracycline/ml and scrolled for 1 hour at 37° C. Subsequently, 100 μl 1% magnetic streptavidin beads were added to the preparations and scrolled for 1 more hour. By means of a magnet (ABgene, Hamburg, DE), the cells bound to the magnetic beads were separated, washed three times with PBST, and determined via their β-galactosidase activity.

14. Living harvest of *E. coli* via the two-step method with biotinylated p12 (FIG. 6):

*E. coli* cells (200 μl of a culture) were harvested according to the two-step method as described in example 9 (10 μg biotinylated p12/ml cell culture and 10 μl 1% streptavidin beads/ml cell culture) and the beads washed twice with PBST. Subsequently, the β-galactosidase activity and the growth of the cells after 2 hours was determined via the scattering at 600 nm in a photometer.

15. Selectivity of the N-strep-p12-dependent harvest (FIGS. 7 and 8):

200 μl each of an overnight culture of different *E. coli* strains (FIG. 7) as well as of different bacteria strains (FIG. 8) were harvested according to the two-step method (as described in example 9). After concentration of the beads in a magnetic separator, the separated cell amount was determined via the scattering of the supernatant at 600 nm.

16. Selective binding of *E. coli* to magnetic streptavidin beads via T4-bio and assay of *E. coli* via FITC-labelled p12 (FIG. 9):

The p12 protein was labelled with FITC (Molecular Probes, Leiden, NL) according to the instructions of the manufacturer and dialysed against PBS. FITC-labelled p12 (5 μg/ml) was added to a mixed culture (about $10^{8-9}$ cells/ml) from *E. coli* and *Serratia marcescens*. After 5 minutes of dark incubation at RT, 109 T4-bio phages and Rifampicin (10 μg/ml), Chloramphenicol (25 μg/ml) and Tetracycline (2 μg/ml) were added. As a control, non-biotinylated T4 phage was added. After an incubation of 10 minutes, 1% streptavidin beads (10 μl/ml) were added and the preparations were studied under a microscope (FIG. 9).

17. Determination of the detection limit for the N-strep-p12-dependent isolation of *E. coli* cells according to the two-step method (FIG. 10):

300 μl each of dilutions of an *E. coli* overnight culture ($10^2$-$10^{15}$ cells/ml) were incubated in microtiter plates with N-strep-p12 (10 μg protein/ml) for 1 hour. Subsequently magnetic streptavidin beads (100 μl 1% beads/ml) were added, mixed, and the bound cells were pelleted by means of a magnet (Bilatek, Mannheim, DE). The beads were washed three times with PBST. The detection of the *E. coli* cells occurred via fluorescence and luminescence substrates for the β-galactosidase.

18. Chemical coupling of T4p12 to magnetic beads (FIG. 11):

150 μl 1% magnetic beads (EM2-100/40, Merck Eurolab, France) were washed three times with 10 mM sodium phosphate buffer, pH 6, resuspended in 40 μl of the buffer. After adding 120 μl EDC-solution (1-Ethyl-3-(3-dimethylamino-propyl)carbodiimide) (30 mg/ml) and incubation for 5 minutes at RT, 160 μl of T4p12 solution (0.7 mg protein/ml 10 mM sodium phosphate buffer, pH 6) was pipetted to the solution, mixed, and the preparation was incubated for 2 hours at RT. By adding 1 volume of 0.2 M Tris-HCl, pH 7, 0.05% Tween 20, the reaction was stopped at 4° C. overnight. The beads were washed subsequently 4 times with PBST and adjusted to 1% with PBST. The coupling of p12 to the beads was determined via a p12-specific antiserum. The binding activity of the p12 beads was determined via the binding of *E. coli* cells according to the one-step method. 3 μl 1% p12 beads were incubated with 200 μl of a hundredfold diluted *E. coli* overnight culture (about $1 \times 10^7$ cells/ml) for 5 minutes, washed three times with PBST, and the bound cells were detected via their β-galactosidase activity (FIG. 11).

19. Adsorption of p12 to different magnetic polyvinylalcohol (PVA) beads (FIG. 12):

200 μl 2% PVA beads (Chemagen, AG, Baesweiler, DE) were incubated with different amounts of T4p12 (0-5 μg protein/mg beads) in 100 mM TrisHCl, pH 8, 1 mM EDTA, 200 mM NaCl overnight at 37° C. The beads were subsequently washed two times with PBST and resuspended in PBS to give 2%. The functional binding of T4p12 to the beads was determined via the binding of *E. coli* cells. 200 μl of an *E. coli* overnight culture were mixed with 10 μl of p12 beads and incubated for 5 minutes at RT. After removal of the bound cells, the scattering of the supernatant was measured at 600 nm and set in relation to the scattering of the *E. coli* culture before adding the beads.

The invention claimed is:

1. A method for the selective purification of bacterial cells or cell components, comprising the following steps:
   a) contacting a sample containing bacterial cells or cell components with isolated bacteriophage proteins;
   b) subsequent incubation of the sample of step a), containing the bacterial cells or cell components and the isolated bacteriophage proteins, with a solid support, wherein the solid support exhibits one or more different coupling group(s) on its surface binding the isolated bacteriophage proteins; and
   c) separating the solid support of step b) with the bacterial cells or cell components bound thereto via the isolated bacteriophage proteins from the sample.

2. The method according to claim 1, wherein the coupling group is a lectin, receptor or anticalin.

3. The method according to claim 1, wherein the coupling group is a streptavidin or Avidin and the isolated bacteriophage proteins are coupled with biotin or a strep-tag.

4. The method according to claim 1, wherein the solid support is a magnetic particle, agarose particle, glass particle, luminex particle, reaction tube, or a microtiter plate.

5. The method according to claim 1, wherein two or more different isolated bacteriophage proteins are added.

* * * * *

UNITED STATES PATENT AND TRADEMARK OFFICE
CERTIFICATE OF CORRECTION

PATENT NO. : 7,579,142 B2  Page 1 of 1
APPLICATION NO. : 10/482235
DATED : August 25, 2009
INVENTOR(S) : Schütz et al.

It is certified that error appears in the above-identified patent and that said Letters Patent is hereby corrected as shown below:

In title page, item (54) Title, delete
"METHODS FOR PURIFICATION OF BACTERIAL CELLS AND COMPONENTS"
and insert
--METHODS FOR PURIFICATION OF BACTERIAL CELLS AND CELL COMPONENTS-- therefor.

In column 1, lines 1-2, delete
"METHODS FOR PURIFICATION OF BACTERIAL CELLS AND COMPONENTS"
and insert
--METHODS FOR PURIFICATION OF BACTERIAL CELLS AND CELL COMPONENTS-- therefor.

Signed and Sealed this

Seventeenth Day of November, 2009

David J. Kappos
*Director of the United States Patent and Trademark Office*

UNITED STATES PATENT AND TRADEMARK OFFICE
CERTIFICATE OF CORRECTION

PATENT NO. : 7,579,142 B2  Page 1 of 1
APPLICATION NO. : 10/482235
DATED : August 25, 2009
INVENTOR(S) : Schütz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1325 days.

Signed and Sealed this

Fourteenth Day of September, 2010

David J. Kappos
*Director of the United States Patent and Trademark Office*

SEQUENCE LISTING

```
<160> NUMBER OF SEQ ID NOS: 8

<210> SEQ ID NO 1
<211> LENGTH: 78
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 1
gaaggaacta gtcatatggc tagctggagc cacccgcagt tcgaaaaagg cgccagtaat    60
aatacatatc aacacgtt                                                  78

<210> SEQ ID NO 2
<211> LENGTH: 54
<212> TYPE: DNA
<213> ORGANISM: Artificial Sequence
<220> FEATURE:
<223> OTHER INFORMATION: Description of Artificial Sequence:  Synthetic
      Primer
```

<400> SEQUENCE: 2
acgcgcaaag cttgtcgacg gatcctatca ttcttttacc ttaattatgt agtt                54

<210> SEQ ID NO 3
<211> LENGTH: 78
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
gaaggaacta gtcatatggc ttgttggagc cacccgcagt tcgaaaaagg cgccagtaat        60
aatacatatc aacacgtt                                                     78

<210> SEQ ID NO 4
<211> LENGTH: 78
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
gaaggaacta gtcatatggc tagctggagc cacccgcagt tcgaaaaagg cgcctgtaat        60
aatacatatc aacacgtt                                                     78

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Met Ala Ser Trp Ser His Pro Gln Phe Glu Lys Gly Ala Ser Asn Asn
1               5                   10                  15

Thr Tyr Gln

<210> SEQ ID NO 6
<211> LENGTH: 19
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Met Ala Cys Trp Ser His Pro Gln Phe Glu Lys Gly Ala Ser Asn Asn
1               5                   10                  15

Thr Tyr Gln

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Met Ala Ser Trp Ser His Pro Gln Phe Glu Lys Gly Ala Cys Asn Asn
1               5                   10                  15

Thr Tyr Gln

<210> SEQ ID NO 8
<211> LENGTH: 539
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

Met Ala Ser Trp Ser His Pro Gln Phe Glu Lys Gly Ala Ser Asn Asn
1               5                   10                  15

Thr Tyr Gln His Val Ser Asn Glu Ser Arg Tyr Val Lys Phe Asp Pro
                20                  25                  30

Thr Asp Thr Asn Phe Pro Pro Glu Ile Thr Asp Val Gln Ala Ala Ile
            35                  40                  45

Ala Ala Ile Ser Pro Ala Gly Val Asn Gly Val Pro Asp Ala Ser Ser
        50                  55                  60

Thr Thr Lys Gly Ile Leu Phe Leu Ala Thr Glu Gln Glu Val Ile Asp
65                  70                  75                  80

Gly Thr Asn Asn Thr Lys Ala Val Thr Pro Ala Thr Leu Ala Thr Arg
                85                  90                  95

Leu Ser Tyr Pro Asn Ala Thr Glu Ala Val Tyr Gly Leu Thr Arg Tyr
                100                 105                 110

Ser Thr Asp Asp Glu Ala Ile Ala Gly Val Asn Asn Glu Ser Ser Ile
            115                 120                 125

Thr Pro Ala Lys Phe Thr Val Ala Leu Asn Asn Val Phe Glu Thr Arg
        130                 135                 140

Val Ser Thr Glu Ser Ser Asn Gly Val Ile Lys Ile Ser Ser Leu Pro
145                 150                 155                 160

Gln Ala Leu Ala Gly Ala Asp Asp Thr Thr Ala Met Thr Pro Leu Lys
                165                 170                 175

Thr Gln Gln Leu Ala Val Lys Leu Ile Ala Gln Ile Ala Pro Ser Lys
            180                 185                 190

Asn Ala Ala Thr Glu Ser Glu Gln Gly Val Ile Gln Leu Ala Thr Val
        195                 200                 205

Ala Gln Ala Arg Gln Gly Thr Leu Arg Glu Gly Tyr Ala Ile Ser Pro
    210                 215                 220

Tyr Thr Phe Met Asn Ser Thr Ala Thr Glu Glu Tyr Lys Gly Val Ile
225                 230                 235                 240

Lys Leu Gly Thr Gln Ser Glu Val Asn Ser Asn Ala Ser Val Ala
                245                 250                 255

Val Thr Gly Ala Thr Leu Asn Gly Arg Gly Ser Thr Thr Ser Met Arg
            260                 265                 270

Gly Val Val Lys Leu Thr Thr Ala Gly Ser Gln Ser Gly Gly Asp
        275                 280                 285

Ala Ser Ser Ala Leu Ala Trp Asn Ala Asp Val Ile His Gln Arg Gly
    290                 295                 300

Gly Gln Thr Ile Asn Gly Thr Leu Arg Ile Asn Asn Thr Leu Thr Ile
305                 310                 315                 320

-continued

```
Ala Ser Gly Gly Ala Asn Ile Thr Gly Thr Val Asn Met Thr Gly Gly
            325                 330                 335

Tyr Ile Gln Gly Lys Arg Val Val Thr Gln Asn Glu Ile Asp Arg Thr
            340                 345                 350

Ile Pro Val Gly Ala Ile Met Met Trp Ala Ala Asp Ser Leu Pro Ser
            355                 360                 365

Asp Ala Trp Arg Phe Cys His Gly Gly Thr Val Ser Ala Ser Asp Cys
            370                 375                 380

Pro Leu Tyr Ala Ser Arg Ile Gly Thr Arg Tyr Gly Gly Ser Ser Ser
385                 390                 395                 400

Asn Pro Gly Leu Pro Asp Met Arg Gly Leu Phe Val Arg Gly Ser Gly
            405                 410                 415

Arg Gly Ser His Leu Thr Asn Pro Asn Val Asn Gly Asn Asp Gln Phe
            420                 425                 430

Gly Lys Pro Arg Leu Gly Val Gly Cys Thr Gly Gly Tyr Val Gly Glu
            435                 440                 445

Val Gln Lys Gln Gln Met Ser Tyr His Lys His Ala Gly Gly Phe Gly
            450                 455                 460

Glu Tyr Asp Asp Ser Gly Ala Phe Gly Asn Thr Arg Arg Ser Asn Phe
465                 470                 475                 480

Val Gly Thr Arg Lys Gly Leu Asp Trp Asp Asn Arg Ser Tyr Phe Thr
            485                 490                 495

Asn Asp Gly Tyr Glu Ile Asp Pro Ala Ser Gln Arg Asn Ser Arg Tyr
            500                 505                 510

Thr Leu Asn Arg Pro Glu Leu Ile Gly Asn Glu Thr Arg Pro Trp Asn
            515                 520                 525

Ile Ser Leu Asn Tyr Ile Ile Lys Val Lys Glu
530                 535
```